US007218766B2

(12) United States Patent
Eberhard et al.

(10) Patent No.: US 7,218,766 B2
(45) Date of Patent: May 15, 2007

(54) COMPUTER AIDED DETECTION (CAD) FOR 3D DIGITAL MAMMOGRAPHY

(75) Inventors: Jeffrey Wayne Eberhard, Albany, NY (US); Abdalmajeid Musa Alyassin, Niskayuna, NY (US); Ajay Kapur, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 660 days.

(21) Appl. No.: 10/121,866

(22) Filed: Apr. 15, 2002

(65) Prior Publication Data

US 2003/0194121 A1  Oct. 16, 2003

(51) Int. Cl.
*C06K 9/00* (2006.01)
(52) U.S. Cl. ........................ 382/132; 382/131; 128/922
(58) Field of Classification Search ................. 382/128, 382/129, 130–132, 181, 190, 195, 224, 225, 382/226, 227, 228, 278, 294, 298, 299
See application file for complete search history.

(56) References Cited

U.S. PATENT DOCUMENTS

| | | | |
|---|---|---|---|
| 3,971,950 A | 7/1976 | Evans et al. | |
| 4,407,163 A | 10/1983 | Hundt et al. | |
| 4,509,368 A | 4/1985 | Whiting et al. | |
| 4,543,959 A | 10/1985 | Sepponen | |
| 4,936,291 A | 6/1990 | Forssmann et al. | |
| 5,003,979 A | 4/1991 | Merickel et al. | |
| 5,133,020 A | 7/1992 | Giger et al. | |
| 5,233,299 A * | 8/1993 | Souza et al. | 324/307 |
| 5,359,513 A * | 10/1994 | Kano et al. | 382/128 |
| 5,361,767 A | 11/1994 | Yukov | |
| 5,474,072 A | 12/1995 | Shmulewitz | |
| 5,479,927 A | 1/1996 | Shmulewitz | |
| 5,603,326 A | 2/1997 | Richter | |
| 5,630,426 A | 5/1997 | Eggers et al. | |
| 5,640,956 A | 6/1997 | Getzinger et al. | |
| 5,660,185 A | 8/1997 | Shmulewitz et al. | |
| 5,664,573 A | 9/1997 | Shmulewitz | |
| 5,735,264 A | 4/1998 | Siczek et al. | |
| 5,776,062 A | 7/1998 | Nields | |
| 5,799,100 A * | 8/1998 | Clarke et al. | 382/132 |
| 5,803,082 A | 9/1998 | Stapleton et al. | |
| 5,810,742 A | 9/1998 | Pearlman | |
| 5,820,552 A | 10/1998 | Crosby et al. | |
| 5,828,774 A | 10/1998 | Wang | |
| 5,832,103 A | 11/1998 | Giger et al. | |

(Continued)

OTHER PUBLICATIONS

A. Thomas Stavros et al.: "Solid Breast Nodules: Use of Sonography to Distinguish between Benign and Malignant Lesions," Radiology, Jul. 1995, pp. 123-134, vol. 196, No. 1, Englewood, CO.

(Continued)

*Primary Examiner*—Shavesh M Mehta
*Assistant Examiner*—Christopher Lavin
(74) *Attorney, Agent, or Firm*—Fletcher Yoder

(57) ABSTRACT

There is provided a method of analyzing a plurality of views of an object, the object including an edge portion partially extending from a surface of the object into an internal volume of the object, comprising the step of analyzing each acquired view. The step of analyzing each acquired view includes analysis of the edge portion. Preferably, the object comprises breast tissue.

38 Claims, 12 Drawing Sheets

U.S. PATENT DOCUMENTS

| | | | |
|---|---|---|---|
| 5,840,022 | A | 11/1998 | Richter |
| 5,851,180 | A | 12/1998 | Crosby et al. |
| 5,855,554 | A | 1/1999 | Schneider et al. |
| 5,872,828 | A | 2/1999 | Niklason et al. |
| 5,938,613 | A | 8/1999 | Shmulewitz |
| 5,983,123 | A | 11/1999 | Shmulewitz |
| 5,984,870 | A | 11/1999 | Giger et al. |
| 5,999,639 | A | 12/1999 | Rogers et al. |
| 6,088,473 | A | 7/2000 | Xu et al. |
| 6,180,943 | B1 | 1/2001 | Lange |
| 6,421,454 | B1* | 7/2002 | Burke et al. ............... 382/131 |
| 6,553,356 | B1* | 4/2003 | Good et al. .................. 706/15 |
| 2001/0010732 | A1 | 8/2001 | Oosawa |

OTHER PUBLICATIONS

Thomas M. Kolb et al.: "Occult Cancer in Women with Dense Breasts: Detection with Screening US-Diagnostic Yield and Tumor Characteristics," Radiology, Apr. 1998, pp. 191-199, vol. 207, No. 1.

Daniel B. Kopans et al.: "Development and Clinical Evaluation of Tomosynthesis for Digital Mammography: Technical and Cost Proposal," Clinical Translational Research Award, Deparment of Defense Breast Cancer Research Program, Nov. 19, 1997, pp. 1-54.

Nico Karssemeijer:"Computer-Aided Detection and Interpretation Mammography," pp. 243-252.

Nico Karssemeijer et al.: "Detection of Stellate Distortions in Mammograms," IEEE Transactions on Medical Imaging, Oct. 1996, pp. 611-619, vol. 15, No. 5, IEEE.

Ioanna Christoyianni et al.: "Fast Detection of Masses in Computer-Aided Mammography," IEEE Signal Processing Magazine, Jan. 2000, pp. 54-64.

Celia Byrne et al.: "Mammographic Features and Breast Cancer Risk: Effects with Time, Age, and Menopause Status," Journal of the National Cancer Institute, Nov. 1, 1995, pp. 1622-1629, vol. 87, No. 21.

Milan Sonka et al.: "Computer-Aided Diagnosis in Mammography," Handbook of Medical Imaging—vol. 2. Medical Image Processing and Analysis, pp. 915-958, Spie Press, Bellingham, Washington.

Matthew A. Kupinski et al.: "Feature Selection and Classifiers for the Computerized Detection of Mass Lesions in Digital Mammography," IEEE Int. Conf. On Neural Nets, 1997, pp. 2460-2463, IEEE.

Shuk-Mei Lai et al.: "On Techniques for Detecting Circumscribed Masses in Mammograms," IEEE Transactions on Medical Imaging, Dec. 1989, pp. 377-386, vol. 8, No. 4, IEEE.

Marios A. Gavrielides et al.: "Segmentation of Suspicious Clustered Microcalcifications in Mammograms," Med. Phys., Jan. 2000, pp. 13-22, vol. 27, No. 1, Am. Assoc. Phys. Med.

Wei Zhang et al: "Optimally Weighted Wavelet Transform Based on Supervised Training for Detection of Microcalcifications in Digital Mammograms," Med. Phys. Jun. 1998, pp. 949-956, vol. 25, No. 6, Am. Assoc. Phys. Med.

Berkman Sahiner et al.: "Computerized Characterization of Masses on Mammograms: The Rubber Band Straightening Transform and Texture Analysis," Med. Phys., Apr. 1998, pp. 516-526, vol. 25, No. 4, Am. Assoc. Phys. Med.

Zhimin Huo et al.: "Computerized Analysis of Mammographic Parenchymal Patterns for Breast Cancer Risk Assessment: Feature Selection," Med. Phys., Jan. 2000, pp. 4-12, vol. 27, No. 1, Am. Assoc. Phys. Med.

Datong Wei et al.: "Classification of Mass and Normal Breast Tissue on Digital Mammograms: Multiresolution Texture Analysis," Med. Phys. Sep. 1995, pp. 1501-1513, vol. 22, No. 9, Am. Assoc. Phys. Med.

John J. Heine et al.: "Multiresolution Statistical Analysis of High-Resolution Digital Mammograms," IEEE Transactions on Medical Imaging, Oct. 1997, pp. 503-515, vol. 16, No. 5, IEEE.

Wouter J. H. Veldkamp et al.: Normalization of Local Contrast in Mammograms, IEEE Transaction on Medical Imaging, Jul. 2000, pp. 731-738, vol. 19, No. 7, IEEE.

Wei Qian et al.: "Tree Structured Wavelet Transform Segmentation of Microcalcifications in Digital Mammography,"Med. Phys., Aug. 1995, pp. 1247-1254, vol. 22, No. 8, Am. Assoc. Phys. Med.

Highnam et al.: "Mammographic Image Analysis," 1999, pp. 39-53, 191-223, Kluwer Academic Publishers.

Duda et al.: "Pattern Classification," 2001, pp. 161-199.

D'Asseler YM et al.: "Recent and Future Evolutions in NeuroSPECT with Particular Emphasis on the Synergistic Use and Fusion of Imaging Modalities," ACTA Neurol. Belg., 1997, pp. 154-162, 97(3) (Abstract Only).

Perault C et al.: "Thoracic and Abdominal SPECT-CT Image Fusion Without External Markers in Endocrine Carcinomas. The Group of Thyroid Tumoral Pathology of Champagne-Ardenne.," J. Nucl. Med., 1997, pp. 1234-1247, 38(8) (Abstract Only).

Web Page http://www.imaging.med.virginia.edu/mbwlab/ct_spect_ms.pdf. Mark B. Williams et al.: "Multimodality Imaging of Small Animals," 1999.

Mark B. Williams et al.: "Integrated CT-SPECT System for Small Animal Imaging," Conf. Rec. IEEE Nuclear Science Symposium/ Medical Imaging Conference, Oct. 15-20, 2000, Lyon, France.

Laura M. Yarusso et al.: "Application of Computer-Aided Diagnosis to Full-Field Digital Mammography," IWDM 2000, 5th International Workshop on Digital Mammography, pp. 421-246, 2001, Medical Physics Publishing, Madison, Wisconsin.

Lihua Li et al.: "Hybrid Classification Method for False-Positive Reduction in CAD for Mass Detection," IWDM 2000, 5th International Workshop on Digital Mammography, pp. 272-279, 2001, Medical Physics Publishing, Madison, Wisconsin.

Robert P. Velthuizen: "Computer Description of Mammographic Masses," IWDM 2000, 5th International Workshop on Digital Mammography, pp. 395-401, 2001, Medical Physics Publishing, Madison, Wisconsin.

Armando Bazzani et al.: "Automatic Detection of Clustered Microcalcifications Using a Combined Method and an SVM Classifier," IWDM 2000, 5th International Workshop on Digital Mammography, pp. 161-167, 2001, Medical Physics Publishing, Madison, Wisconsin.

Yoshihito Hagihara et al.: "Accurate Detection of Microcalcifications on Mammograms by Improvement of Morphological Processing," IWDM 2000, 5th International Workshop on Digital Mammography, pp. 193-197, 2001, Medical Physics Publishing, Madison, Wisconsin.

M. Lanyi: "Diagnosis and Differential Diagnosis of Microcalcifications," pp. 44, 60, 61, 86, 95, 98-101, 110, 118-120 and 192, 1987, Springer-Verlag.

Daniel B. Kopans: "The Positive Predictive Value of Mammography," AJR, Mar. 1992, pp. 521-526, vol. 158, American Roentgen Ray Society.

J. I. Hasegawa et al., "Automated Extraction 1-10 of Lung Cancer Lesions from Multislice Chest Ct Images by Using Three-dimensional Image Processing", *Systems & Computers in Japan, Scripta Technica Journals*, vol. 25, No. 11, Oct. 1, 1994, pp. 68-76.

* cited by examiner

COMPUTER AIDED DETECTION (CAD) FOR 3D DIGITAL MAMMOGRAPHY

STATEMENT REGARDING FEDERALLY SPONSORED RESEARCH & DEVELOPMENT

The government may have rights in this invention pursuant to Subcontract 22287 issued from the Office of Naval Research/Henry M. Jackson Foundation.

BACKGROUND OF THE INVENTION

The present invention relates generally to analyzing digital imaging, and more particularly to computer aided detection (CAD) of abnormalities in a three dimensional (3D) mammography method, system, and apparatus.

It is well know in the medical community that breast cancer is a leading cause of death in women (and to a lesser extent also affects men). When early detection of abnormalities is combined with proper medical attention, however, the risk of death and/or severe medical ramifications can be drastically reduced. Many devices and techniques (e.g., mammography) are currently under development to detect breast abnormalities earlier, and with greater accuracy than conventional devices. A brief summary of some conventional devices, techniques, and their limitations follows.

Presently, the vast majority of mammography devices utilize conventional x-ray techniques. A patient's breast is positioned in an x-ray machine, which passes x-rays through the breast and generates a corresponding x-ray image on a film. The film is then analyzed by a trained clinician, who examines the film for abnormalities, such as a mass, a cyst, a microcalcification, a fibrous finding, an architectural distortion, and/or other abnormal findings related with benign or malignant abnormalities. In standard digital mammography, the x-ray image (or projection radiograph) is acquired by means of a digital detector, and the resulting digital image can be processed to enhance the visibility of structures within the image, thus providing a potentially more useful image to the clinician. These standard mammography techniques, however, suffer from many problems.

One problem with film based mammography can be generally referred to as film saturation. To fully penetrate through dense parts of the breast, a higher dose of radiation is utilized, generally on the order of about 3 Gy. In relatively dense parts of the breast, a sizeable amount of the radiation is absorbed by the dense tissue, the residual radiation exposing the film. Due to the large x-ray absorption within the dense tissue, the film is not saturated by too much residual radiation, and thus provides sufficient contrast for detecting abnormalities. Near the edges of the breast (e.g. near the skin surface), however, the higher dose of radiation is absorbed to a lesser extent, thus a higher amount of residual radiation exposes the film, which results in film saturation. Film saturation can lead to lower contrast (if any at all) especially near the edges of the breast, and may hinder the clinician's ability to properly identify an abnormality.

Furthermore, the 2D nature of standard mammography techniques (including standard digital and film based) also leads to superposition (e.g., overlay) problems. Superposition can occur when multiple structures are overlaid onto the same position in the projection image. The overlaid normal (i.e., non-malignant) structures may end up combining in appearance to appear as an abnormality, resulting in a "false positive" identification of an abnormality. Presently, the false positive rate is relatively high: on the order of between 70% and 90% of biopsies are normal. Conversely, real abnormalities may be superimposed over dense tissue regions which "hide" the abnormality within the dense tissue, resulting in a "false negative" miss of an abnormality. Thus, in standard 2D imaging (e.g., projection radiography) structures within the breast may become superimposed with each other, thereby normal structures within the breast can "interfere" with a clear interpretation of structures of interest (e.g., potentially malignant) which are located at a different height (relative to the projection direction) within the imaged object.

Another problem with many mammography techniques is related to contrast and structural orientation issues. Radiation passing through the breast is used to generate a view of the breast. "Image slices" of the breast are then generated from multiple views using conventional or newly developed algorithms. As used herein "image slice" is a single image representative of the structures within an imaged object (e.g., breast tissue) at a fixed height above the detector. Abnormalities having a substantial size in the direction approximately parallel to the detector surface will thus generally appear in the image with sufficient contrast and size to be detected by a trained clinician. Abnormalities having a relatively small size in the direction approximately parallel to the detector surface (e.g., a thin duct running substantially perpendicular to the detector surface), however, may only appear as a very small dot in the image. The "dot" like appearance of abnormalities that do not run substantially parallel to the detector surface may hinder the clinician's ability to properly identify an abnormality.

Another problem with conventional mammography techniques is directly related to the importance of having trained and experienced clinicians examining the image (e.g., the film). Without proper training (or even through inadvertence of a trained clinician), abnormalities may be missed, especially when they are relatively small or low contrast in appearance. Moreover, even a well trained clinician generally will not always be able to fully analyze the image in view of previous mammograms and/or patient history (e.g., family history, prior mammograms, health history, lifestyle history, etc.) due to time considerations, fatigue, etc., such that the clinician may not always catch a progression of tissue growth or tissue changes that would be more apparent when considering the additional information.

On inspection of mammograms by a clinician, sometimes radiologists identify suspicious regions (e.g., abnormalities) and request follow up examinations of the breast with ultrasound, nuclear medicine and/or further diagnostic x-rays. The follow up ultrasound and/or nuclear medicine examinations, however, are generally conducted on an entirely different machine than the mammography device, these machines commonly having an entirely different patient configuration and/or image acquisition geometry for different modalities. It is thus difficult (if even possible) to spatially correlate image acquisitions from other modalities with the mammograms. Thus, there is some uncertainty as to whether the follow up scan locates and characterizes the same region. Indeed, it has been estimated that at least 10% of the masses that were identified on ultrasound scans as corresponding to the mammographically suspicious regions were found to correspond to very different regions in the breast. In fact, this percentage is expected to be significantly higher in patients with dense breasts.

Thus, a need exists for an improved method and apparatus for the detection of abnormalities within tissue.

BRIEF SUMMARY OF THE INVENTION

The present invention is directed at improving and/or eliminating one or more of the problems set forth above, and other problems found within the prior art.

According to one aspect of the present invention, a method of analyzing a plurality of views of an object is provided, the object including an edge portion partially extending from a surface of the object into an internal volume of the object, comprising the step of analyzing each acquired view. The step of analyzing each acquired view includes analysis of the edge portion.

According to another aspect of the present invention, a program product for causing a machine to analyze a plurality of views from a tomosynthesis system is provided, the tomosynthesis system imaging an object including an edge portion partially extending from a surface of the object into an internal volume of the object, the program product causing the machine to perform the step of analyzing each acquired view. The step of analyzing each acquired view includes analysis of the edge portion.

According to another aspect of the present invention, a tissue imaging device is provided comprising a radiation source for emitting radiation through tissue to be imaged, the radiation source being angularly displaceable through a plurality of emission positions corresponding to a plurality of views, a detector positioned to detect radiation emitted through the tissue, the detector generating a signal representing an view of the tissue, and a processor electrically coupled to the detector for analyzing the signal. The processor analyzes each acquired view, the analysis including analysis of an edge portion of the tissue partially extending from a surface of the tissue into an internal volume of the tissue.

According to another aspect of the present invention, a method of analyzing an object with a multi-modality imaging system is provided comprising the steps of detecting a region of concern in at least one of a first image of the object generated by a first modality and a second image of the object generating by a second modality, classifying the detected region of concern, correlating the region of concern with a corresponding region in the other of the first image and the second image, and weighting the classification with a weighting factor corresponding to a degree of correlation. The first modality is different from the second modality. Preferably, the first image and the second image are fused together. More preferably, the first image is registered with the second image, and differences in spacial resolution between the first image and the second image is corrected.

According to another aspect of the present invention, an imaging system for imaging an object is provided comprising means for generating a first image of the object from x-ray radiation, means for generating a second image of the object from ultrasound, means for detecting a region of concern in at least one of the first image and the second image, means for correlating the detected region of concern with a corresponding region in the other of the first image and the second image, means for at least one of determining whether the abnormality is present in the corresponding region in the other of the first image and the second image and comparing at least one of a shape of the detected region of concern, a size of the detected region of concern, a contrast of the detected region of concern, and a contrast distribution of the detected region of concern, means for classifying the abnormality and means for weighting the classification in relation to a degree of correlation.

DETAILED DESCRIPTION OF THE INVENTION

Reference will now be made in detail to presently preferred embodiments of the present invention. Wherever possible, the same reference numbers will be used throughout the drawings to refer to the same or like parts.

The present invention will be described in reference to apparatuses and methodology for breast imaging and breast cancer detection. It should be appreciated, however, that the teachings of the present invention may also be used in other areas, such as lung imaging, brain imaging, liver imaging, kidney imaging, bone imaging, and other medical areas, as well as in industrial applications, such as detecting low density regions in fabricated parts, or performing fault/fatigue testing (e.g., examining for cracks, depressions, or impurities).

In recent years, research into improved imaging systems for breast cancer detection has focused on digital imaging systems, and more particularly, to digital imaging systems with automated abnormality detection and risk analysis. A two part article entitled "Mammographic Tissue, Breast Cancer Risk, Serial Image Analysis, and Digital Mammography" by John J. Hein, PhD, which is incorporated by reference herein in its entirety, provides a review of breast tissue-risk research, and its application to digital mammography.

3D digital tomosynthesis is one such new x-ray imaging system that creates 3D digital images of tissue (e.g., breast tissue). A suitable tomosynthesis device is described in copending application entitled "Tomosynthesis X-Ray Mammogram System And Method With Automatic Drive System" which is incorporated by reference herein in its entirety. Another suitable tomosynthesis device is described in U.S. Pat. No. 5,872,828 which is also incorporated by reference herein in its entirety.

Figure 1:
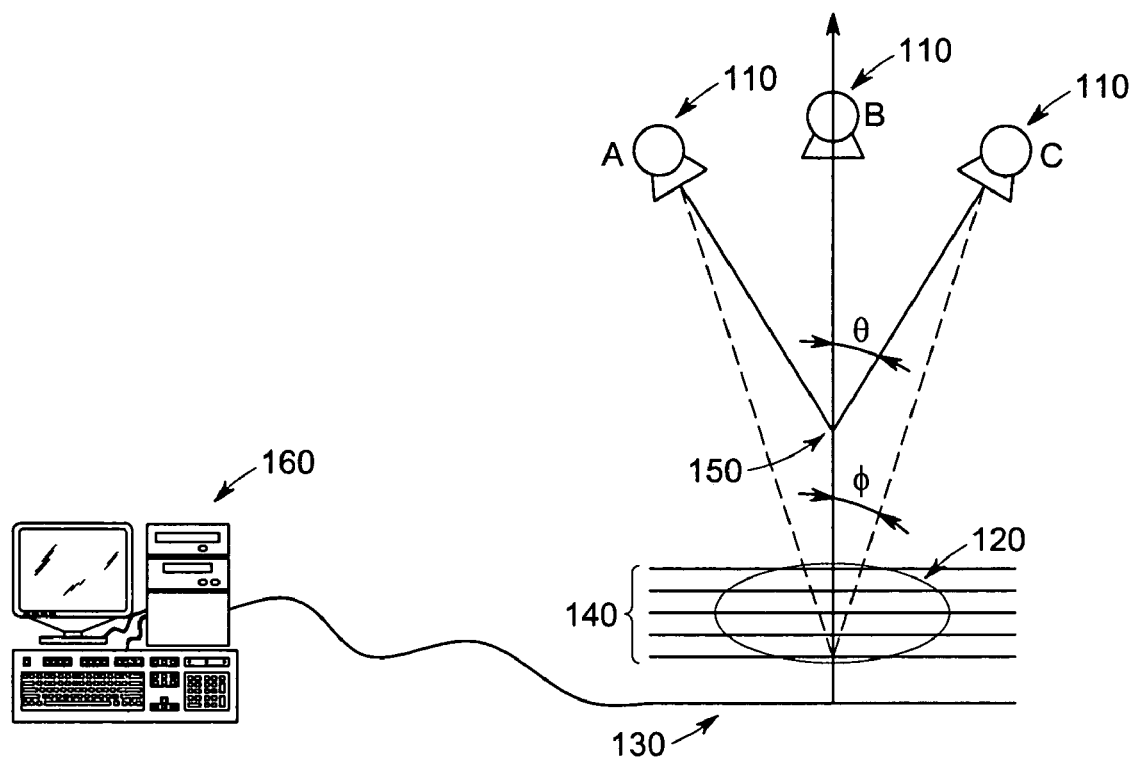
FIG. 1 is a block diagram of a tomosynthesis device according to an embodiment of the present invention.

A tomosynthesis device according to one embodiment of the present invention is shown in FIG. 1. A radiation source 110 for emitting x-ray radiation is angularly displaceable through a plurality of emission positions A, B, C corresponding to a plurality of views of the tissue 120. While only three emission positions are shown in FIG. 1, one of ordinary skill in the art will recognize that three emission positions or fewer or more emission positions may be utilized, while remaining within the scope of the invention. The radiation source 110 is angularly displaceable so as to enable acquisition of radiographs of the breast from different projection angles. This can be achieved, for example, by angularly displacing the radiation source 110 about a pivot point 150, preferably about 15cm above the breast tissue. The radiation source 110 is angularly displaceable through a projection angle A, which is preferably less than ±180°. Preferably, A is in the range of less than about ±45°, and most preferably less than about ±30°. More preferably, at least 11 emission positions are used, and spaced at about constant angular spacings. In the system configuration of FIG. 1, the projection angle A is generally significantly smaller than the "gantry angle" A. The projection angle A is essentially given by the angle of a ray of the beam passing through the "center" of the object, with reference to some "zero-degree" angle. Unlike in computed tomography (CT) scanning, the radiation source 110 is preferably not angularly displaceable all the way around the breast tissue 120.

A detector 130 is positioned substantially opposite of the radiation source 110, with respect to the imaged object 120 to detect radiation emitted through the tissue 120, the detector generating a signal representing a view of the tissue 120. Preferably, the detector 130 is positioned less than about 25 cm (most preferably about 22.4 cm) below the pivot point 150. The signal is transmitted to a computer 160, including a processor for analyzing the view (and reconstructing image slices 140). Preferably, the computer is part of a tomosynthesis device including the radiation source 110 and the detector 130. Alternatively, the signal may be stored on a storage media or transmitted to a central computer system, and later analyzed by computer 160. Such a configuration may occur, for example, with a mobile tomosynthesis system that takes data of a patient's breast at a remote site, which is later analyzed at a laboratory.

Other tomosynthesis system configurations are also plausible, as would be readily apparent to one of ordinary skill in the art after reading this disclosure. One such system may employ a radiation source movable along a track rather than on a rotating gantry, preferably with a radiation source to detector distance in the range of about 100 cm to about 180 cm. The aforementioned configurations have been provided for purposes of illustration only, and are not limiting on the scope of this application.

The 3D data set (i.e., image(s)) taken by the tomosynthesis system are processed by a computer aided detection (CAD) device (i.e., computer 160), to take advantage of the significant increase in information available in 3D data sets over conventional 2D data sets. In this way, the advantages of 3D data are combined with the conventional 2D images to achieve a new, higher level of performance in mammography imaging as will be described in greater detail below.

Improved performance is at least partially related to the fact that the image data is acquired at various orientations A, B, C with respect to the breast 120 and any pathology it may contain. This allows better separation of true structure from superimposed tissue, correlation of information in different acquisition positions, correlation of spatial structures in the 3D image sets, and 3D specific processing for enhanced performance.

The inventors have discovered, however, that the signal:to:noise ratio (SNR) per view for tomosynthesis tends to be lower than in conventional film/screen mammography due to the larger number of acquisitions without substantially increasing the patient's exposure to radiation for health concerns. The ability to reconstruct 3D images, reduce structure noise, and reduce the implication of superpositioning far outweighs the disadvantages (e.g., lower SNR performance) which would teach away from using a tomosynthesis technique. Furthermore, the advantages of having a large dynamic range and a priori knowledge of the detector and system characteristic also provides greater advantages than the foreseeable disadvantages which would teach away from using this approach. Specific examples of methodology to achieve this improved performance is set forth below.

Figure 2:
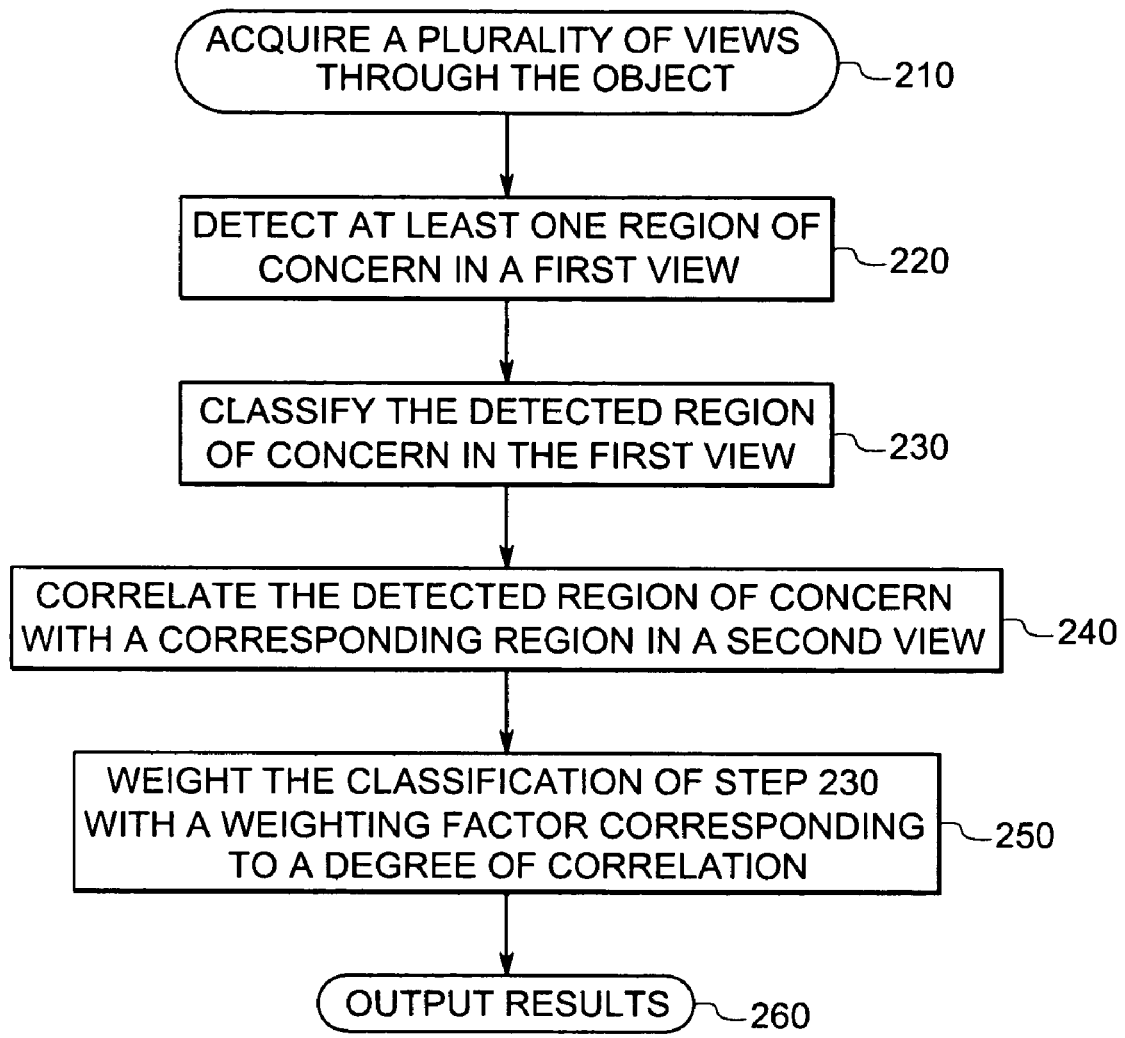
FIG. 2 is a flow chart of a method of analyzing an image according an embodiment of the present invention.

FIG. 2 depicts a block diagram of a method of analyzing a plurality of views of breast tissue according to an embodiment of the present invention. The method can be performed, for example, by a computer workstation for processing data from a tomosynthesis device, or by a processor within a tomosynthesis device itself.

In step 210, a tomosynthesis device acquires a plurality of views through breast tissue or any other object to be imaged. Step 210 can be performed in a manner as described in the aforementioned copending applications. The plurality of views are then sent to a processor for analysis.

In step 220, the processor detects at least one region of concern in a first view (if such a region exists). If the processor detects at least one region of concern, the processor then classifies the detected region of concern (e.g., as a mass, a cyst, a microcalcification, etc.) in step 230 using a new or conventional algorithm. Exemplary algorithms can be found, for example, in "Application of Computer-Aided Diagnosis to Full-Field Digital Mammography" by L M Yarusso et. al, which is incorporated by reference herein in its entirety. The processor then correlates the detected region of concern with a corresponding region in a second view in step 240. Preferably, the processor correlates the detected region of concern with a corresponding region in a plurality of other views in step 240.

Figure 6:
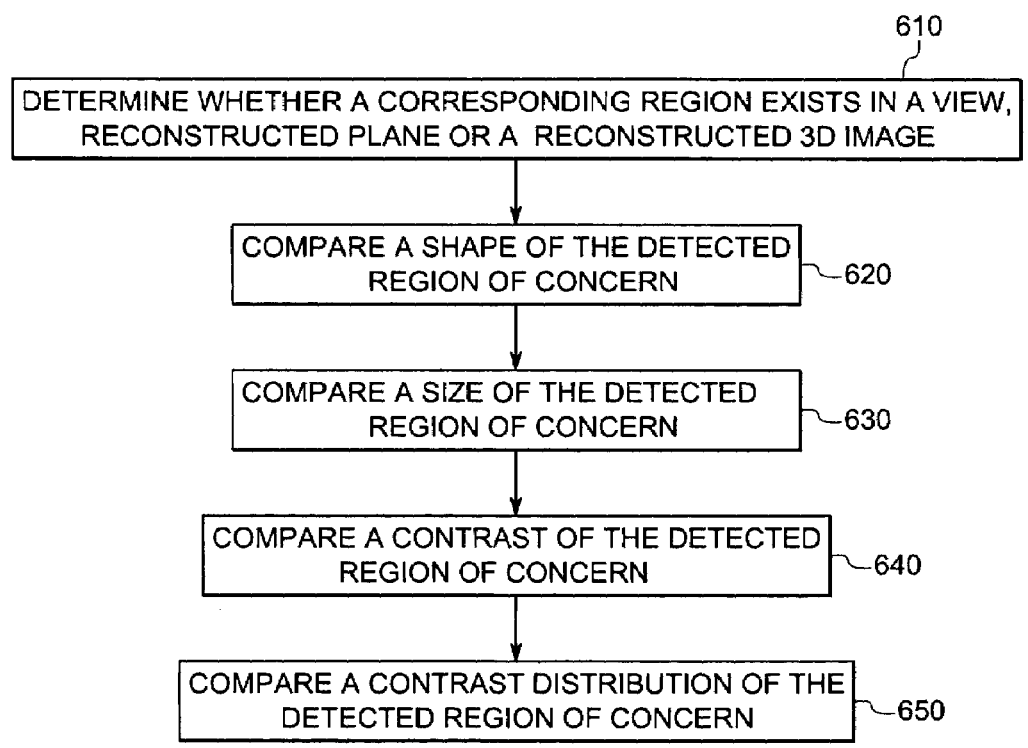
FIG. 6 is a flow chart of a method including various correlating steps according an embodiment of the present invention.

The processor then weights the classification of step 230 with a weighting factor corresponding to a degree of correlation in step 250. As referred to herein, the term "degree of correlation" relates to the similarity of one image to another image. Thus, if the degree of correlation is high, this represents greater confidence that the classified region is classified correctly. As shown in FIG. 6, for example, correlating may comprise at least one of steps 610, 620, 630, 630, 640 and 650. In step 610, the processor determines whether a corresponding region exists in any other view, reconstructed plane (as will be described below), or reconstructed 3D image (as will be described below). Thus, if no corresponding region exists, there is a low probability that the region of concern is, in fact, an abnormality at all and the classification is weighted accordingly. Furthermore the shape of the detected region of concern (step 620), the size of the detected region of concern (step 630), the contrast of the detected region of concern (step 640), the contrast distribution of the detected region of concern (step 650), and the correlation with the same in a corresponding region can be individually or in combination used to weight the classification with a weighting factor corresponding to a degree of correlation.

The results of the analysis are then outputted in step 260. Step 260 may comprise, for example, selectably displaying the information as described in copending application entitled "Method and Apparatus For Providing Mammographic Image Metrics To A Clinician" which is incorporated by reference herein in its entirety. Other output methods are also plausible, as would be readily apparent to one of ordinary skill in the art after reading this disclosure.

Figure 3:
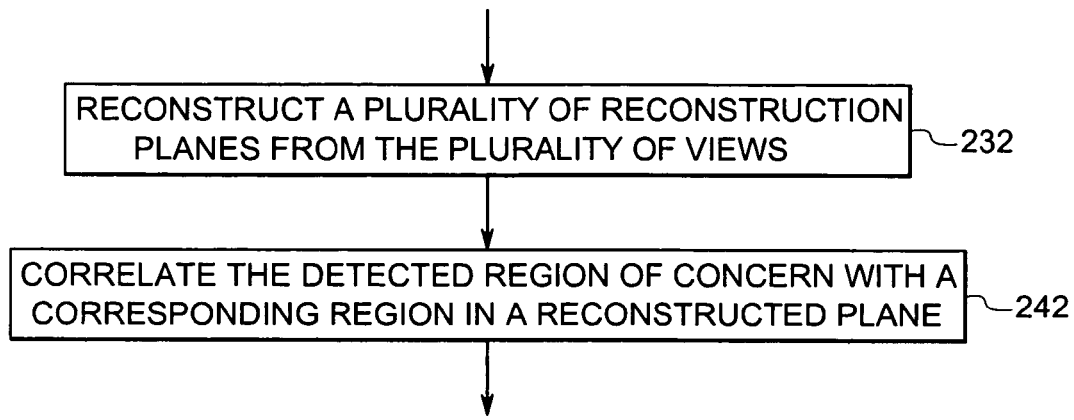
FIG. 3 is a flow chart of a method of analyzing an image including reconstruction according an embodiment of the present invention.

As shown in FIG. 3, the processor preferably also reconstructs a plurality of reconstruction planes from the plurality of views in step 232. Reconstruction planes may include, for example, (i) image slices parallel to the detector 130 (i.e., substantially perpendicular to the z-axis); (ii) planes substantially perpendicular to the x and y axis; and (iii) oblique planes at any orientation in the 3D volume. Reconstruction techniques as used in "Limited-Data Computed Tomography Algorithms for the Physical Sciences" by D. Verhoeven which is incorporated by reference herein in its entirety, may, for example, be used for this approach.

Preferably, the processor then correlates the detected region of concern from step 220 with a corresponding region in a reconstruction plane in step 242. Step 242 can be performed in a similar fashion as described above for step 240. Alternatively, step 242 can be performed in place of step 240.

Figure 4:
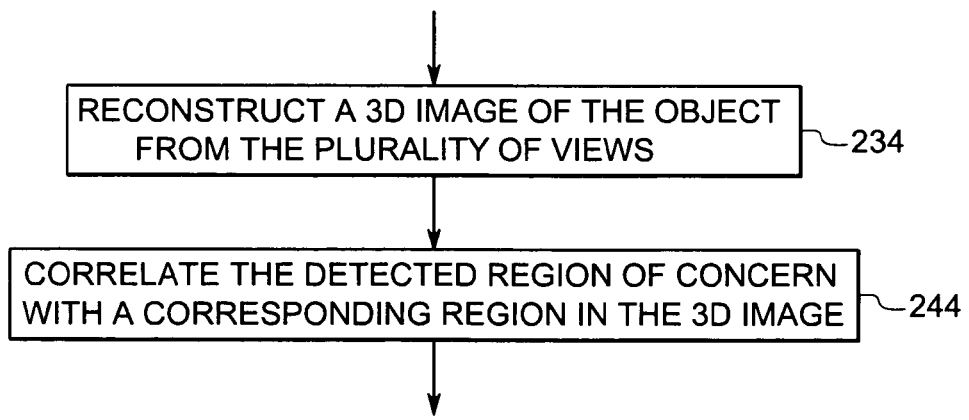
FIG. 4 is a flow chart of a method of analyzing an image including reconstructing a 3D image according an embodiment of the present invention.

As shown in FIG. 4, the processor preferably also reconstructs a 3D image of the breast from the plurality of views in step 234. Step 234 can be performed, for example, as described in copending application entitled "Generalized Filtered Back-Projection Reconstruction In Digital Tomosynthesis", which is incorporated by reference herein in its entirety. Preferably, the processor then correlates the detected region of concern from step 220 with a corresponding region in the 3D image in step 244. Step 244 can be performed in a similar fashion as described above for step 240. Alternatively, step 244 can be performed in place of step 240.

Figure 5:
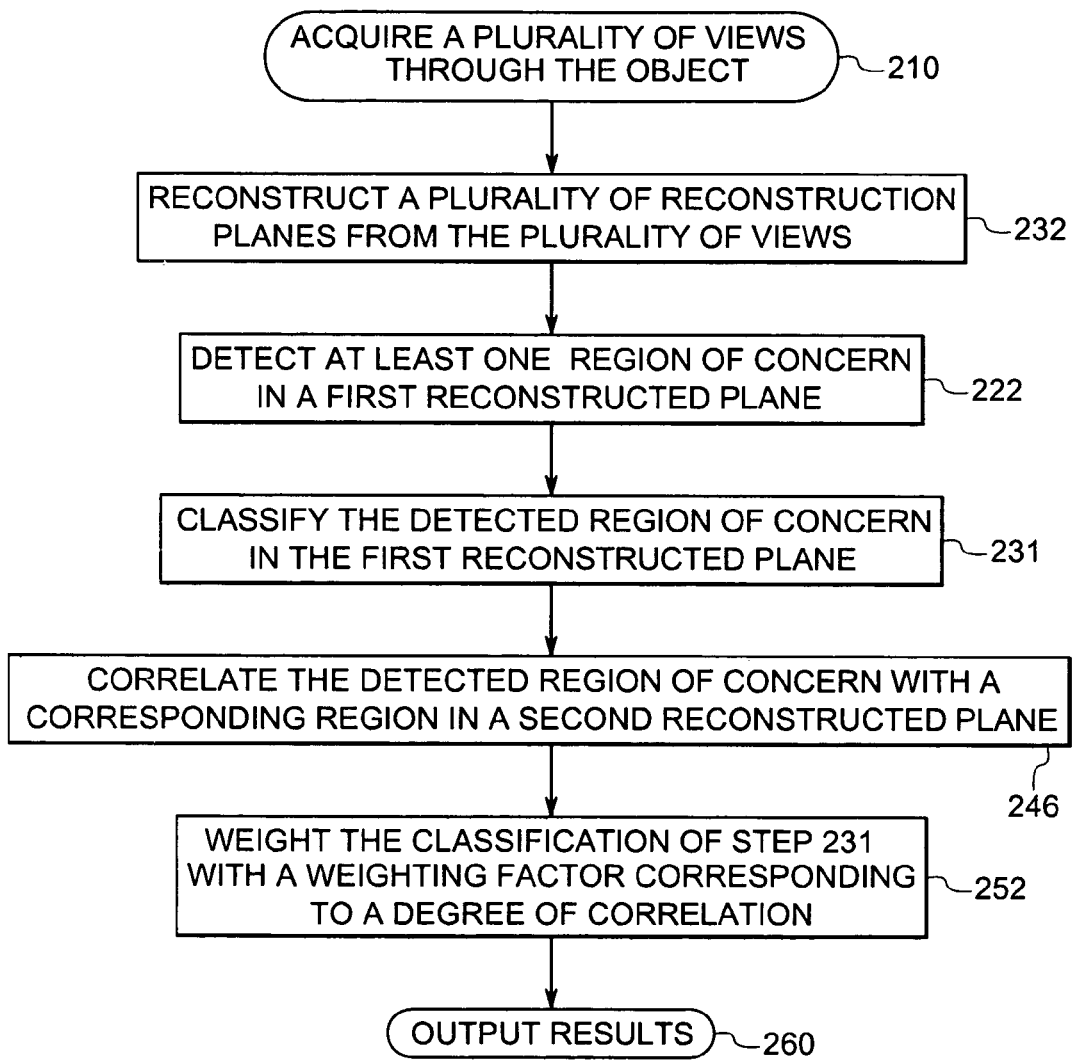
FIG. 5 is a flow chart of a method of analyzing an image including reconstruction according an embodiment of the present invention.

As would be readily apparent to one of ordinary skill in the art after reading this disclosure, detection step 220 and classification step 230 can also be performed directly on a reconstructed plane and/or on the reconstructed 3D image, rather than directly on a view or in combination therewith. Thus, as shown in FIG. 5, for example, the processor need not perform steps 220, 230, 240, and 250 (i.e., view analysis) if the processor performs steps 222, 231, 246, and 252 (i.e., reconstructed plane analysis). Similarly, the processor may only perform reconstructed 3D image analysis if desired. In a preferred embodiment, however, the processor performs view analysis, reconstructed plane analysis, reconstructed 3D image analysis, and combinations thereof to achieve a higher degree of performance.

Figure 7:
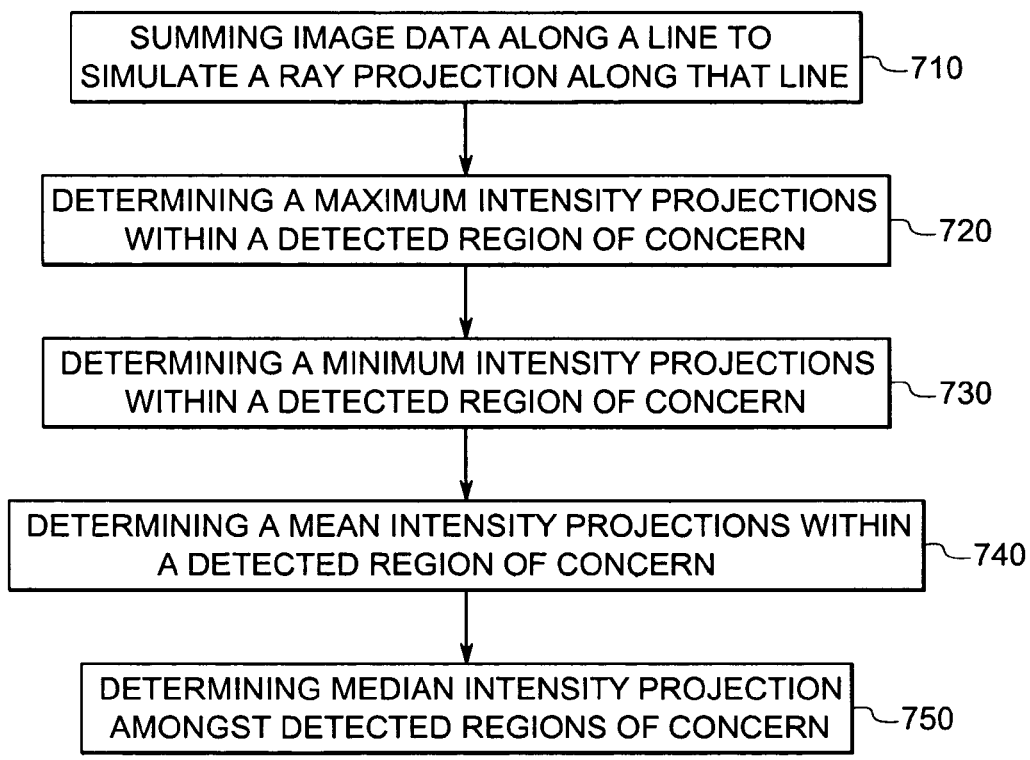
FIG. 7 is a flow chart of a method of analyzing a reconstructed 3D image according an embodiment of the present invention.

Additional analysis can be taken on the reconstructed 3D image as shown, for example, in FIG. 7. In step 710, image data along a line may be summed to simulate a ray projection along that line. In step 720, a maximum intensity projection within a detected region of concern can be determined. In step 730, a minimum intensity projection within a detected region of concern can be determined. In step 740, a mean intensity projection within a detected region of concern can be determined. In step 750, a median intensity projection amongst detected regions of concern can be determined. Steps 710, 720, 730, 740, and 750 can be performed individually, in combination, and/or with other steps using new or conventional techniques, and thereby provide additional analysis tools to achieve an even higher degree of performance.

In the above described embodiment, the 2D projection data acquired at the individual angles in the tomosynthesis acquisition scan can be used to more accurately detect pathologies. The correlations between the views, the reconstructed planes, and/or the reconstructed 3D image enhances detection by confirming that the location of a particular "finding" (i.e., a classified abnormality) in a projection at one angle is well defined in some or all others as well. In addition, the size of the finding, its contrast, its contrast distribution, etc. can all be used in combination or individually as described to determine the correlation of these parameters in different projections. The probability of a finding being important is increased as the correlation of the parameters in the different projections increases. Thus, the number of "false positive" identifications can be effectively decreased, while simultaneously reducing the number of "false negative" identifications.

Furthermore, the reconstructed planes tend to have a more limited range of data, which eases detection of pathologies since voxel values (i.e., 3D boxes at each reference point within a reconstructed 3D image) are more directly related to feature characteristics, and less to the geometry of the imaging. Moreover, volumetric information can be considered in the classification of pathologies in the reconstructed 3D image, such as taking neighborhood information into account. This allows characterization of the full volume of the finding directly. Full volume characterization can be particularly beneficial in detecting long, thin, string-like features, where the continuity of the structure in the "string direction" could be lost in a 2D analysis. String detection loss in 2D analysis is especially prevalent if the analysis planes are perpendicular to the string direction, and noise, for example, interrupts the tracing of the 3D length of the feature.

The detection described above can be done on the data directly, or after image processing to enhance specific features. In addition, image processing to reduce or remove certain artifacts specific to the tomosynthesis acquisition geometry can be used. Spatial resolution of the image can also be modified in the processing. Specifically, the data can be down sampled or interpolated to change the effective voxel size, to improve performance or reduce computational load. Searches for findings can be done in a multi-resolution fashion, with initial searches for larger findings done on a coarser grid, and finer searches for smaller findings done on higher resolution image sets. This down sampling or interpolation may be particularly appropriate in the z-direction, where the spatial resolution of the tomosynthesis images is inherently the largest. Methods which make use of multiple views or 3D reconstructed images generally benefit from improved SNR compared to single projection methods.

The probability that a finding is of interest can be assigned by using a weighted combination of results as described. In this way, all the information can be combined in the most effective way to increase the sensitivity and specificity of the results. SNR and spatial localization information can also be used in determining the proper weighting. These probabilities can also be correlated with patient age, health history, tissue type in the breast, tissue type in the neighborhood of finding, knowledge about pathology type and morphology (e.g., minimum number of microcalcifications in a cluster before it is deemed important) and other key parameters to improve performance, as CAD allows for automatic computation and consideration of many parameters in addition to the data sets generated by the tomosynthesis device.

Furthermore, the entire process can be automated in a CAD device to reduce the dependency on trained and experienced clinicians. This too will improve accuracy and reduce the number of false positive and false negative classifications.

Additional improvements are also plausible as would be readily apparent to one of ordinary skill in the art after reading this disclosure. According to a preferred embodiment, the tomosynthesis device further includes an imaging device operating at a different modality (e.g., ultrasound, nuclear medicine, etc.) as will be described in detail below. It should be appreciated that the above described features may also apply to the multi-modality imaging device described below.

Figure 8:
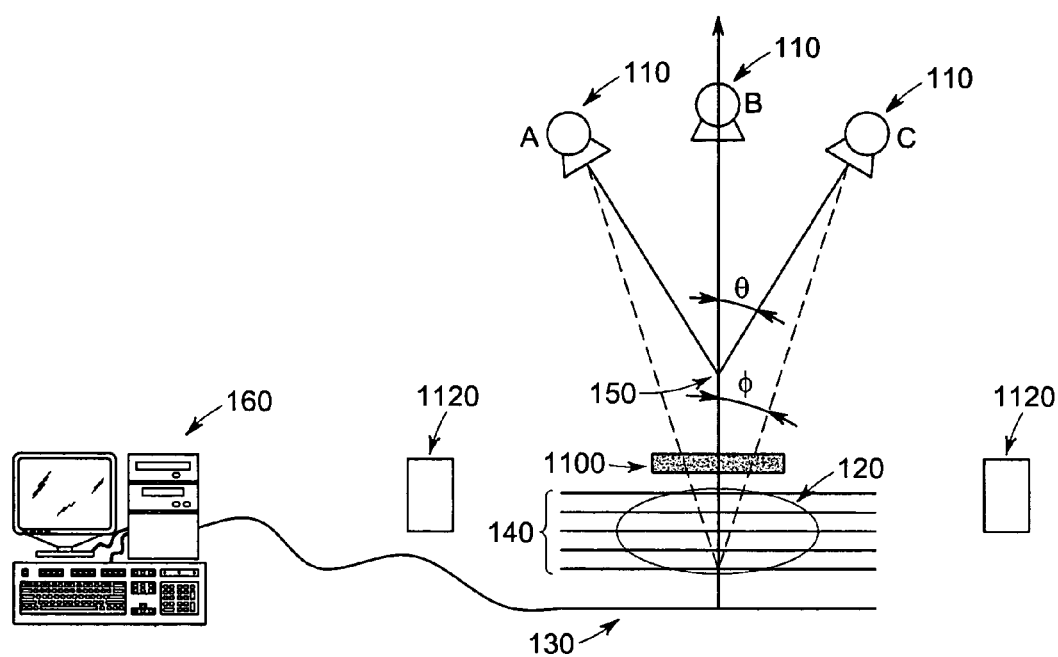
FIG. 8 is a block diagram of a multi-modality imaging device according to an embodiment of the present invention.

A multi-modality imaging device according to an embodiment of the present invention is shown in the block diagram of FIG. 8. A similar device is the subject of copending application entitled "Combined Digital Mammography And Breast Ultrasound System" which is incorporated by reference herein in its entirety. As shown in FIG. 8, one or more of an ultrasound emitting device 1100 and/or a plurality of nuclear medicine detectors 1120 are provided as additions to the tomosynthesis device of FIG. 1. Preferably, ultrasound emitting device 1100 is applied after x-ray imaging takes place, so as to not adversely affect the x-ray imaging of the tissue 120. The positioning and number of ultrasound emitting devices 1100 and nuclear medicine detectors 1110 (e.g., gamma radiation detectors) can be adjusted as would be readily apparent to one of ordinary skill in the art after reading this disclosure. The specific methodology of a multi-modality system will be described below.

Figure 9:
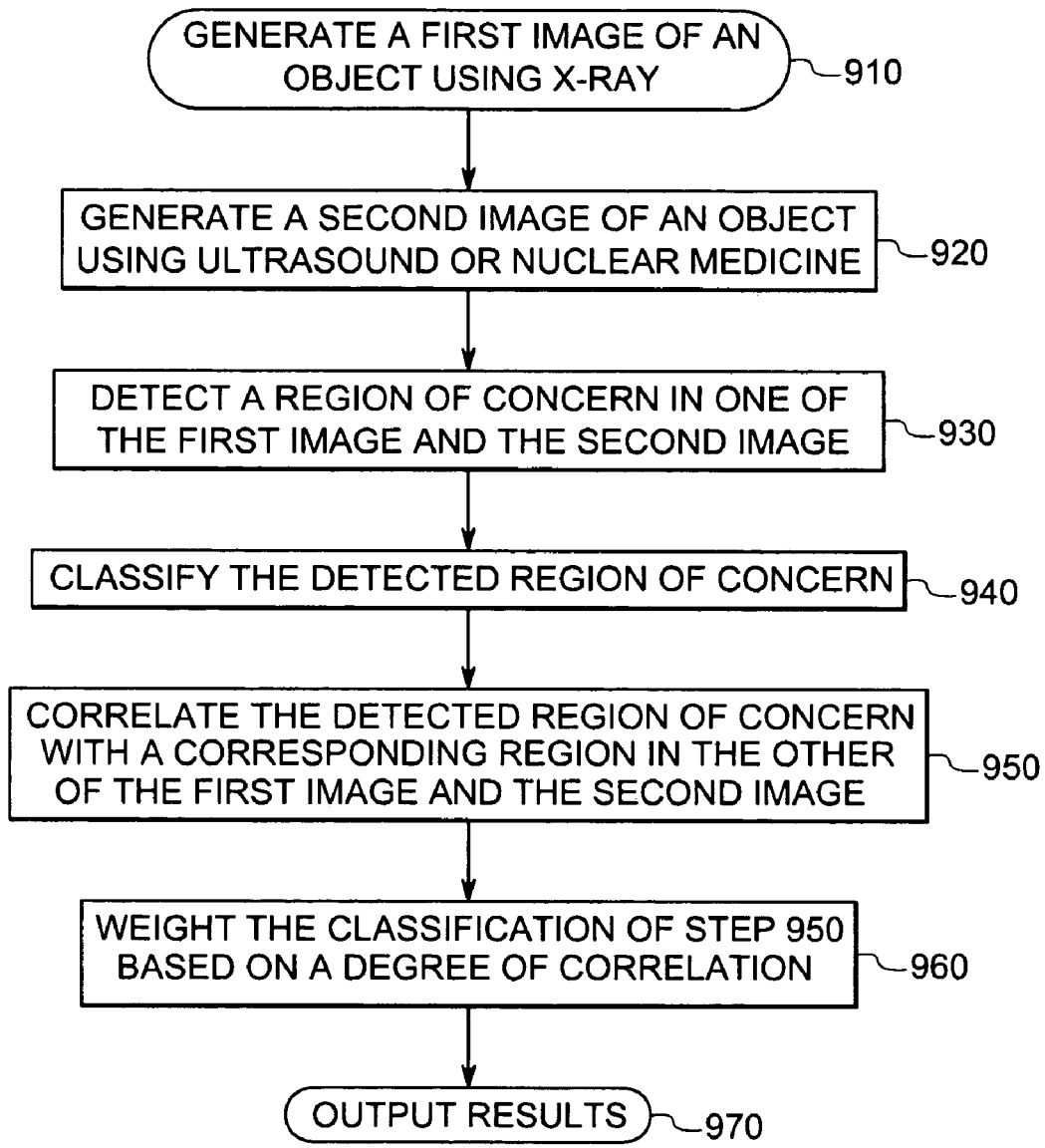
FIG. 9 is a flow chart of a method of analyzing an image according an embodiment of the present invention.

A method of analyzing an object with a multi-modality imaging system according to an embodiment of the present invention is shown in the flow chart of FIG. 9. A first image of the object (preferably a 3D image) is generated using an x-ray modality in step 910. A second image of the object (preferably a 3D image) is generated in step 920 using a different modality (e.g, ultrasound or nuclear medicine). Steps 910 and 920 may be performed as described in copending applications. The remaining description of this embodiment will be described specifically in reference to an x-ray/ultrasound multi-modality system. However, the disclosure similarly applies to other modalities including nuclear medicine (e.g., single photon emission computed tomography (SPECT) or positron emission tomography (PET)), etc. Preferably, the object being imaged in steps 910 and 920 is restrained in substantially the same position during image acquisition (e.g., by a compression device such as a compression paddle).

In step 930, a region of concern is detected in at least one of the first image and the second image. Step 930 can be similarly performed as described for step 220. As shown in FIGS. 10–13, for example, mass 10 and cyst 20 can be seen in both the x-ray image (Tomo) and the ultrasound image (US). Thus, step 930 may detect, for example, either the mass 10, the cyst 20, or both in either the Tomo image, the US image, or both. It should also be appreciated that detecting a region of concern in the Tomo image may detect a region of concern in a view, a reconstructed plane, and/or a reconstructed 3D image as previously described. Similarly, detecting a region of concern in the ultrasound image may detect a region of concern in a view, an image plane, and/or a 3D image.

The detected region of concern is then classified in step 940 (e.g., classified as a cyst, a mass, a microcalcification, etc.). The detected region of concern is then correlated with a corresponding region in the other of the first image and second image in step 950. Correlating may include, for example, steps similar to steps 610, 620, 630, 640, and 650 in FIG. 6 but for modality to modality in addition to multiple views (e.g., views, reconstructed planes, reconstructed 3D image, etc.) within a given modality. The classification is then weighted in step 960 based on a degree of correlation. The results of the analysis are then outputted in step 970.

Figure 10:
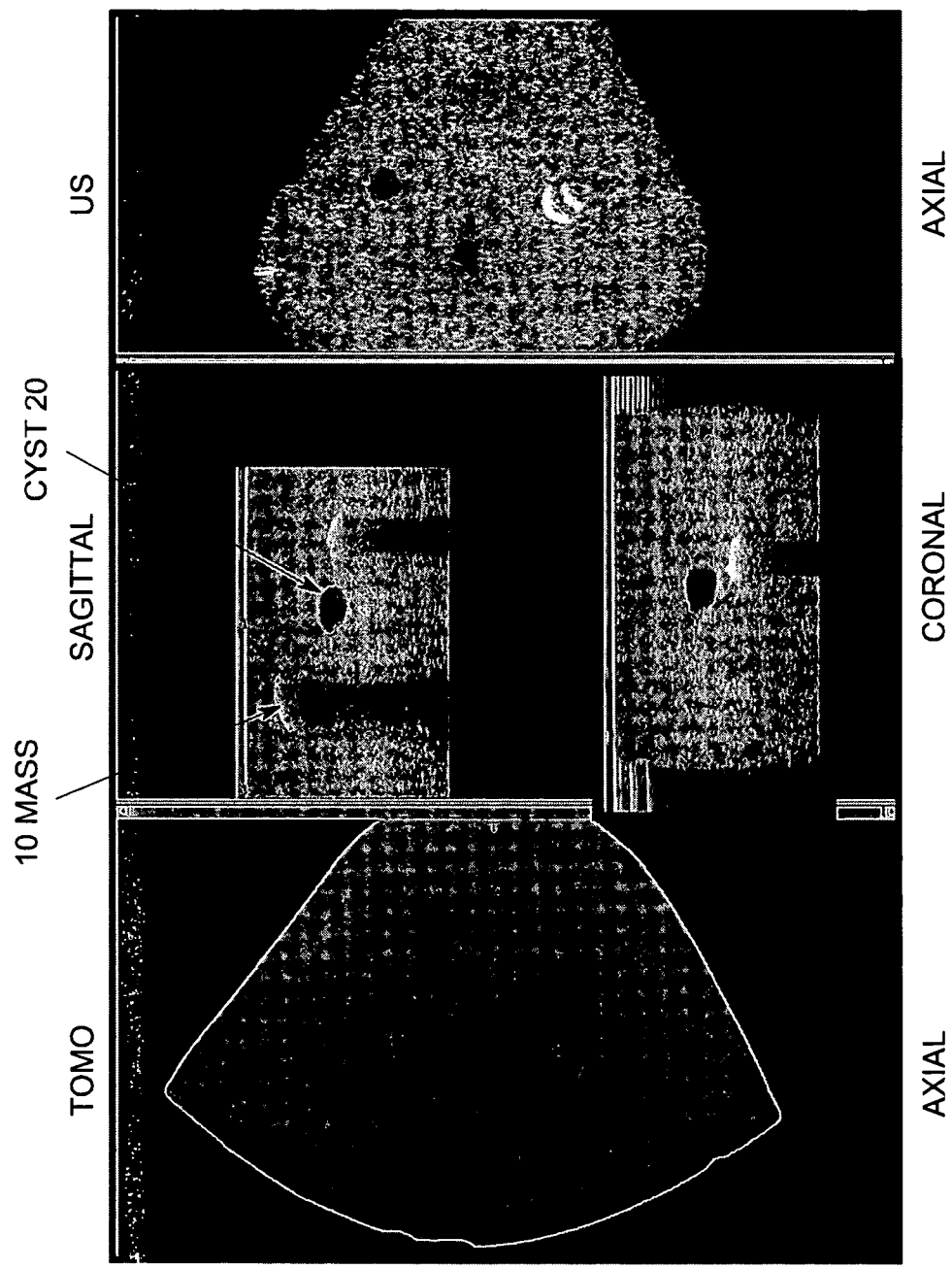
FIGS. 10–13 depict an image from tomosynthesis and/or ultrasound acquisition according an embodiment of the present invention.
Figure 11:
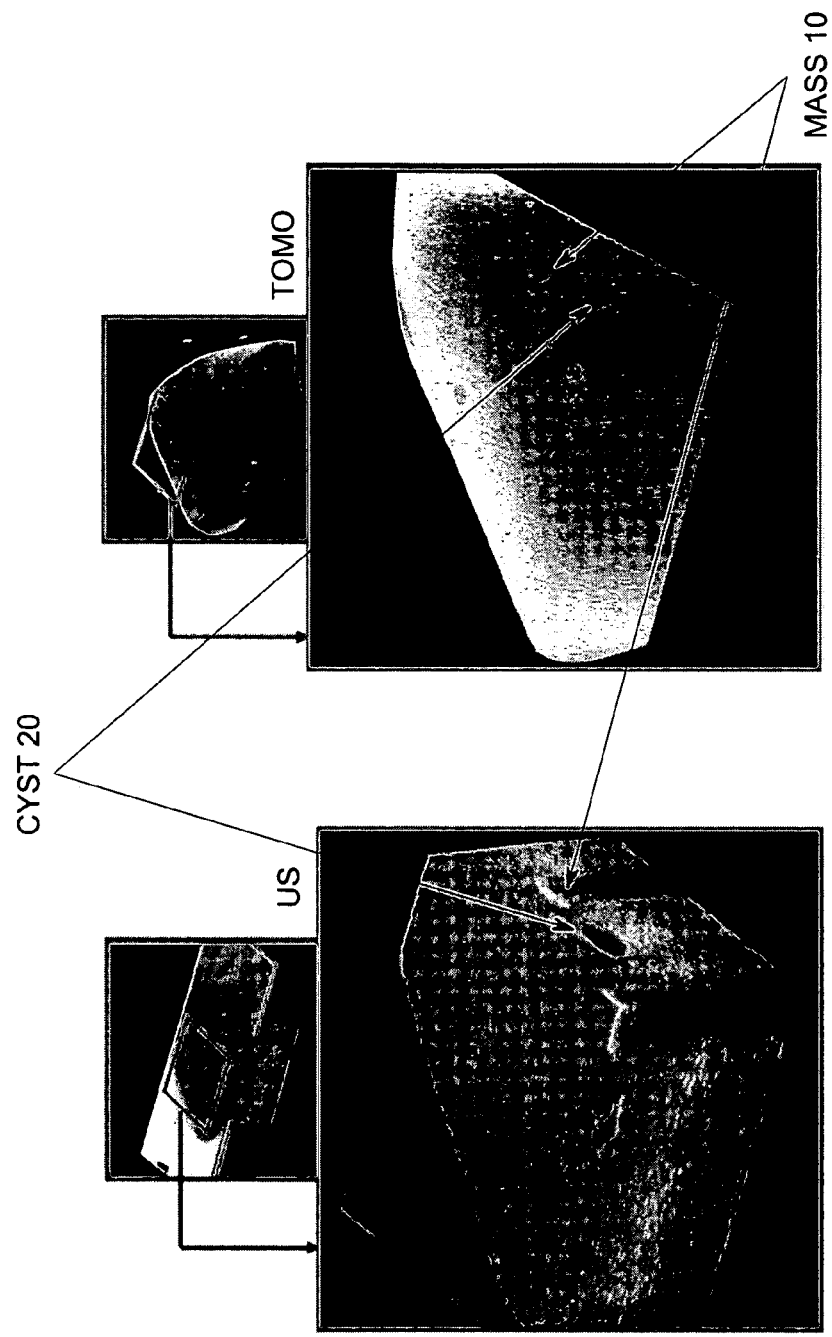
Figure 12:
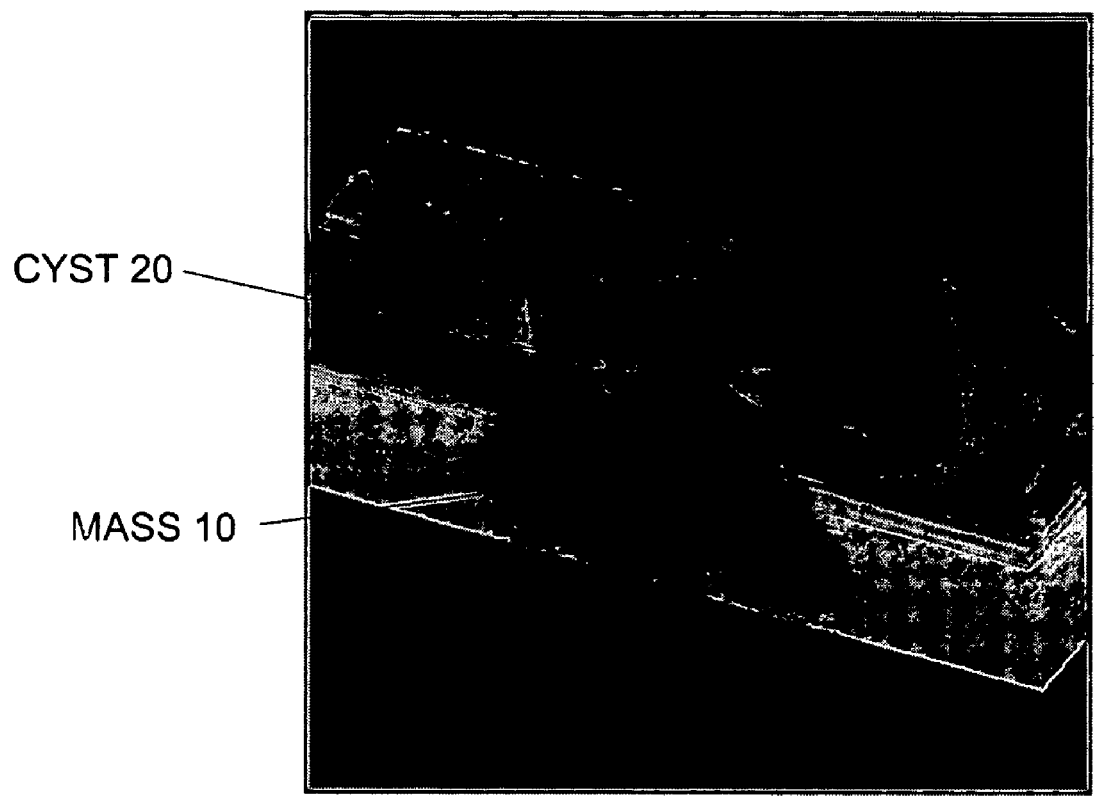
Figure 13:
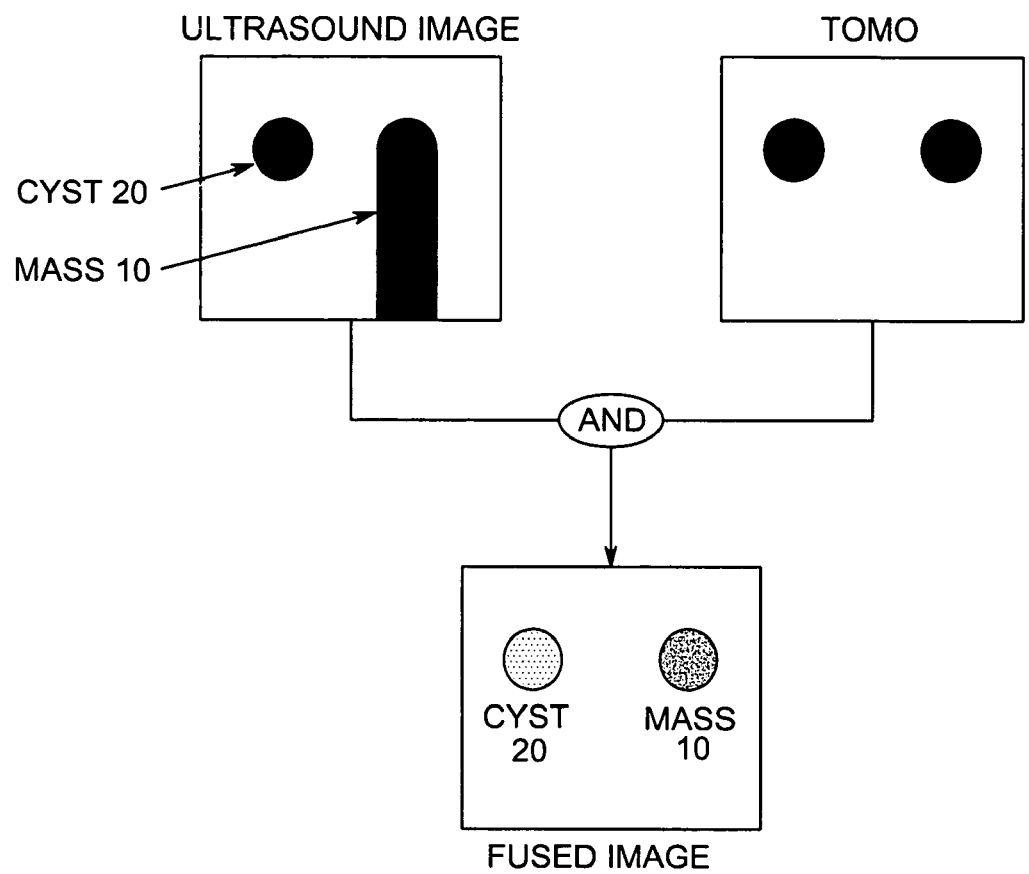

The inventors have found considerable advantages from utilizing the above described multi-modality approach in addition to the advantages described above for other embodiments of the present invention. In general, the use of supplementing modalities (i.e., in addition to x-ray) provides for much greater data to analyze the object to be imaged. For example, conventional x-ray devices tend to have high resolution in planes parallel to the detector surface as can be seen in FIG. 10. However, x-ray devices tend to have a much lower resolution in planes perpendicular to the detector surface, as shown in FIG. 11. Generally, the resolution for ultrasound depends on the orientation of the transducer relative to the x-ray detector, the resolution being generally lower in the direction in which the transducer is swept. Thus, preferably, the ultrasound acquisition is arranged to have low resolution in planes parallel to the detector surface (FIG. 10), and high resolution in planes perpendicular to the detector surface (FIG. 11) to achieve high resolution in planes where the x-ray resolution is relatively low. This arrangement can be achieved by positioning the transducer perpendicular to the x-ray detector and above the breast. By this configuration, an overall improvement in resolution can be achieved simply by combining these two approaches.

Moreover, the overall confidence in classifications (i.e., a reduction in false negative and false positive identifications) can be dramatically improved by correlating detection of abnormalities across multiple modalities as described, as different modalities tend to detect different characteristics of objects better than others. Improved classification can also be achieved by detecting abnormalities directly in a fused image (see FIG. 13) with greater overall resolution in all directions. Thus, by correlating detecting regions of concern within a given modality or between different modalities, or by analyzing a region of concern within a fused image, the overall performance of image analysis can be improved.

It should be noted that although the flow chart provided herein shows a specific order of method steps, it is understood that the order of these steps may differ from what is depicted. Also two or more steps may be performed concurrently or with partial concurrence. Such variation will depend on the software and hardware systems chosen, which is generally considered a matter of designer choice. It is understood that all such variations are within the scope of the invention. Likewise, software and web implementation of the present invention could be accomplished with standard programming techniques with rule based logic and other logic to accomplish the various database searching steps, correlation steps, comparison steps and decision steps.

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method of analyzing a plurality of angularly displaced views of an object, comprising the steps of:
   analyzing each of at least three angularly displaced views including a plurality of x-ray image data collected at different angular positions of the radiation source with respect to the object, wherein the step of analyzing each acquired view comprises detecting at least one region of concern; and classifying said detected region of concern;

correlating a detected region of concern in a first view of said plurality of angularly displaced views with a corresponding region in a second view of said plurality of angularly displaced views; and weighting said classification with a weighting factor corresponding to a degree of correlation.

2. The method of claim 1, wherein said object comprises breast tissue, and wherein the step of classifying said detected region of concern classifies pathologies within said breast tissue.

3. The method of claim 1, wherein the step of correlating comprises at least one of:

determining that a corresponding region does not exist; and comparing at least one of:
 a shape of the detected region of concern;
 a size of the detected region of concern;
 a contrast of the detected region of concern; and
 a contrast distribution of the detected region of concern.

4. The method of claim 1, further comprising a step of reconstructing a plurality of reconstructed planes from said plurality of angularly displaced views.

5. The method of claim 4, further comprising the steps of:

detecting at least one region of concern in a reconstructed plane; and classifying said detected region of concern in the reconstructed plane.

6. The method of claim 5, further comprising the steps of:

correlating a detected region of concern in a first reconstructed plane of said plurality of reconstructed planes with at least one of:

a corresponding region in a second reconstructed plane of said plurality of reconstructed planes;

a corresponding region in at least one of said plurality of angularly displaced views; and weighting said classification with a weighting factor corresponding to a degree of correlation.

7. The method of claim 1, further comprising a step of reconstructing a three dimensional (3D) image of said object from said plurality of angularly displaced views.

8. The method of claim 7, further comprising the steps of:

detecting regions of concern in said reconstructed 3D image; and classifying said detected regions of concern in said reconstructed 3D image.

9. The method of claim 8, further comprising the steps of:

correlating a detected region of concern in said 3D image with a corresponding region in at least one view of said plurality of angularly displaced views; and weighting said classification with a weighting factor corresponding to a degree of correlation.

10. The method of claim 8, further comprising at least one of the steps of:

summing image data along a line to simulate a ray projection along that line;

determining maximum intensity projections within a detected region of concern;

determining a minimum intensity projection within a detected region of concern;

determining a mean intensity projection within a detected region of concern; and determining median intensity projection amongst said detected regions of concern.

11. The method of claim 1 wherein said plurality of angularly displaced views are acquired with an x-ray modality, further comprising the steps of:

correlating said detected region of concern with a corresponding region in an image acquired by one of an ultrasound modality and a nuclear medicine modality; and weighting said classification with a weighting factor corresponding to a degree of correlation.

12. The method of claim 11, wherein the step of correlating comprises at least one of:

determining that a corresponding region does not exist; and comparing at least one of:
 a shape of the detected region of concern;
 a size of the detected region of concern;
 a contrast of the detected region of concern; and
 a contrast distribution of the detected region of concern.

13. The method of claim 1, further comprising the steps of:

angularly displacing a radiation source about a pivot point to a position corresponding to said view;

radiating said object via said radiation source; and detecting radiation from said object.

14. A program product recorded on a computer readable medium for causing a machine to analyze a plurality of angularly displaced views from a tomosynthesis system, said tomosynthesis system imaging an object, said program product causing the machine to perform the steps of:

analyzing each of at least three angularly displaced views including a plurality of x-ray image data collected at different angular positions of the radiation source with respect to the object wherein the step of analyzing each acquired view comprises detecting at least one region of concern; and classifying said detected region of concern;

correlating a detected region of concern in a first view of said plurality of angularly displaced views with a corresponding region in a second view of said plurality of angularly displaced views; and weighting said classification with a weighting factor corresponding to a degree of correlation.

15. The program product of claim 14, further causing the machine to perform the step of:

reconstructing a plurality of reconstructed planes from said plurality of angularly displaced views.

16. The program product of claim 15, further causing the machine to perform the steps of:

detecting at least one region of concern in a reconstructed plane; and classifying said detected region of concern in the reconstructed plane.

17. The program product of claim 16, further causing the machine to perform the steps of:

correlating a detected region of concern in a first reconstructed plane of said plurality of reconstructed planes with at least one of:

a corresponding region in a second reconstructed plane of said plurality of reconstructed planes;

a corresponding region in at least one of said plurality of angularly displaced views; and weighting said classification with a weighting factor corresponding to a degree of correlation.

18. The program product of claim 16, wherein said plurality of angularly displaced views are acquired with an x-ray modality, further causing the machine to perform the steps of:

correlating said detected region of concern with a corresponding region in an image acquired by one of an ultrasound modality and a nuclear medicine modality; and weighting said classification with a weighting factor corresponding to a degree of correlation.

19. The program product of claim 14, further causing the machine to perform the step of reconstructing a three dimensional (3D) image of said object from said plurality of angularly displaced views.

20. The program product of claim 19, further causing the machine to perform the steps of:
detecting regions of concern in said reconstructed 3D image; and
classifying said detected regions of concern in said reconstructed 3D image.

21. The program product of claim 20, further causing the machine to perform the steps of:
correlating a detected region of concern in said 3D image with a corresponding region in at least one view of said plurality of angularly displaced views; and
weighting said classification with a weighting factor corresponding to a degree of correlation.

22. The program product of claim 14, further causing the machine to perform the steps of:
angularly displacing a radiation source about a pivot point to a position corresponding to said view;
radiating said object via said radiation source; and
detecting radiation from said object.

23. A tissue imaging device, comprising:
a radiation source for emitting radiation through tissue to be imaged, said radiation source being angularly displaceable through a plurality of emission positions corresponding to a plurality of angularly displaced views;
a detector positioned to detect radiation emitted through said tissue, said detector generating a signal representing an angularly displaced view of said tissue, wherein the angularly displaced view includes x-ray image data collected at a different angular positions of the radiation source with respect to the tissue; and
a processor electrically coupled to said detector for analyzing said signal, wherein said processor analyzes at least three of said plurality of angularly displaced views by detecting at least one region of concern classifying, said detected region of concern, correlating a detected region of concern in a first view of said plurality of angularly displaced views with a corresponding region in a second view of said plurality of angularly displaced views and weighting said classification with a weighting factor corresponding to a degree of correlation.

24. The tissue imaging device of claim 23, wherein said processor further:
reconstructs a plurality of reconstructed planes from said plurality of angularly displaced views.

25. The tissue imaging device of claim 24, wherein said processor further:
detects at least one region of concern in a reconstructed plane; and
classifies said detected region of concern in the reconstructed plane.

26. The tissue imaging device of claim 25, wherein said processor further:
correlates a detected region of concern in a first reconstructed plane of said plurality of reconstructed planes with at least one of:
a corresponding region in a second reconstructed plane of said plurality of reconstructed planes;
a corresponding region in at least one of said plurality of angularly displaced views; and
weights said classification with a weighting factor corresponding to a degree of correlation.

27. The tissue imaging device of claim 23, wherein said processor further:
reconstructs a three dimensional (3D) image of said object from said plurality of angularly displaced views.

28. The tissue imaging device of claim 27, wherein said processor:
detects regions of concern in said reconstructed 3D image; and
classifies said detected regions of concern in said reconstructed 3D image.

29. The tissue imaging device of claim 28, wherein said processor further:
correlates a detected region of concern in said 3D image with a corresponding region in at least one view of said plurality of angularly displaced views; and
weights said classification with a weighting factor corresponding to a degree of correlation.

30. The tissue imaging device of claim 23, wherein the radiation source is angularly displaceable through less than 360° about said tissue.

31. The tissue imaging device of claim 23, further comprising one of:
an ultrasound imager comprising:
an ultrasound source for emitting ultrasound through tissue to be imaged;
an ultrasound detector positioned to detect ultrasound emitted through said tissue to generate an ultrasound image;
a nuclear medicine detector to generate a nuclear medicine image, wherein said processor further:
detects a region of concern in said plurality of angularly displaced views;
correlates said detected region of concern with a corresponding region in one of said ultrasound image and said nuclear medicine image; and
weights said classification with a weighting factor corresponding to a degree of correlation.

32. A method of analyzing an object with a multi-modality imaging system, comprising the steps of:
generating a plurality of angularly displaced views of said object by a first modality, wherein each of the plurality of angularly displaced views includes x-ray image data collected at different angular positions of a radiation source with respect to said object;
detecting a region of concern in at least three of the plurality of angularly displaced views of said object generated by the first modality and a second image of said object generated by a second modality;
classifying said detected region of concern;
correlating said region of concern with a corresponding region in other of said angularly displaced views and said second image; and
weighting said classification with a weighting factor corresponding to a degree of correlation, wherein said first modality is different from said second modality.

33. The method of claim 32, wherein said first modality and said second modality each comprises one of x-ray, ultrasound, and nuclear medicine.

34. The method of claim 32, wherein at least one of said angularly displaced view and said second image comprise a three dimensional (3D) reconstructed image of said object.

35. The method of claim 32, further comprising at least one of:
- determining that a corresponding region does not exist; and
- comparing at least one of:
  - a shape of the detected region of concern;
  - a size of the detected region of concern;
  - a contrast of the detected region of concern; and
  - a contrast distribution of the detected region of concern.

36. The method of claim 32, further comprising the step of:
- fusing said angularly displaced view with said second image.

37. The method of claim 32, further comprising the steps of:
- registering said angularly displaced view with said second image; and correcting differences in spatial resolution between said angularly displaced view and said second image.

38. An imaging system for imaging an object, comprising:
- means for generating at least one of a plurality of angularly displaced views of said object from x-ray radiation;
- means for generating a second image of said object from ultrasound;
- means for detecting a region of concern in at least three of said angularly displaced views and said second image;
- means for classifying said detected region of concern;
- means for correlating said detected region of concern with a corresponding region in other of said angularly displaced views and said second image;
- means for at least one of:
  - determining whether said abnormality is present in said corresponding region in said other of said angularly displaced view and said second image; and comparing at least one of:
  - a shape of the detected region of concern;
  - a size of the detected region of concern;
  - a contrast of the detected region of concern; and
  - a contrast distribution of the detected region of concern;
- means for classifying said abnormality; and
- means for weighting said classification in relation to a degree of correlation.

* * * * *